(12) United States Patent
Shah et al.

(10) Patent No.: US 7,682,367 B2
(45) Date of Patent: Mar. 23, 2010

(54) SURGICAL STAPLING APPARATUS

(75) Inventors: Sachin Shah, Milford, CT (US); John Beardsley, Wallingford, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 0 days.

(21) Appl. No.: 11/712,849

(22) Filed: Feb. 28, 2007

(65) Prior Publication Data

US 2008/0203134 A1 Aug. 28, 2008

(51) Int. Cl.
*A61B 17/068* (2006.01)
*A61B 17/10* (2006.01)

(52) U.S. Cl. ............... 606/139; 227/181.1; 227/178.1; 227/177.1

(58) Field of Classification Search .............. 227/176.1, 227/177.1, 178.1, 181.1; 606/139
See application file for complete search history.

(56) References Cited

U.S. PATENT DOCUMENTS

| | | | | |
|---|---|---|---|---|
| 4,429,695 | A | * | 2/1984 | Green ..................... 227/176.1 |
| 4,508,253 | A | * | 4/1985 | Green ......................... 227/19 |
| 5,040,715 | A | * | 8/1991 | Green et al. ............. 227/176.1 |
| 5,307,976 | A | * | 5/1994 | Olson et al. .............. 227/175.3 |
| 5,312,023 | A | | 5/1994 | Green et al. |
| 5,381,943 | A | | 1/1995 | Allen et al. |
| 5,456,401 | A | | 10/1995 | Green et al. |
| 5,485,952 | A | | 1/1996 | Fontayne |
| 5,560,532 | A | * | 10/1996 | DeFonzo et al. ......... 227/176.1 |
| 5,601,224 | A | | 2/1997 | Bishop et al. |
| 5,704,534 | A | * | 1/1998 | Huitema et al. .......... 227/175.1 |
| 5,713,505 | A | | 2/1998 | Huitema |
| 5,725,536 | A | | 3/1998 | Oberlin et al. |
| 5,762,256 | A | * | 6/1998 | Mastri et al. ............. 227/176.1 |
| 5,779,132 | A | | 7/1998 | Knodel et al. |
| 5,820,009 | A | | 10/1998 | Melling et al. |
| 5,823,066 | A | | 10/1998 | Huitema et al. |
| 5,901,895 | A | | 5/1999 | Heaton et al. |
| 6,010,054 | A | | 1/2000 | Johnson et al. |
| 6,663,641 | B1 | | 12/2003 | Kovac et al. |
| 6,786,382 | B1 | | 9/2004 | Hoffman |

(Continued)

FOREIGN PATENT DOCUMENTS

DE 19951940 6/2001

(Continued)

OTHER PUBLICATIONS

European Search Report for EP 08075145.6-1265 date of completion is Apr. 25, 2008 (10 pages).

*Primary Examiner*—Rinaldi I. Rada
*Assistant Examiner*—Gloria R. Weeks (57) ABSTRACT

A surgical stapling apparatus, including a frame, an endoscopic portion, a clamp handle, a firing handle, a tool assembly and a drive beam is disclosed. The endoscopic portion extends distally from the frame. The clamp handle is disposed on the frame and in mechanical cooperation with a drive member. The firing handle is disposed on the frame and in mechanical cooperation with at least one firing rod. The tool assembly includes an anvil, a cartridge assembly and a camming surface and is supported adjacent a distal end of the endoscopic portion. Actuation of the clamp handle moves the drive beam into engagement with the camming surface. Actuation of the firing handle moves the firing rod through an opening in the drive beam to eject surgical fasteners from the cartridge assembly.

22 Claims, 6 Drawing Sheets

U.S. PATENT DOCUMENTS

| | | |
|---|---|---|
| 6,877,647 B2 | 4/2005 | Green et al. |
| 6,978,921 B2 * | 12/2005 | Shelton et al. ........... 227/176.1 |
| 2002/0099372 A1 | 7/2002 | Schulze et al. |
| 2005/0006430 A1 | 1/2005 | Wales |
| 2005/0006431 A1 | 1/2005 | Shelton, IV et al. |
| 2005/0006432 A1 | 1/2005 | Racenet et al. |
| 2005/0096694 A1 | 5/2005 | Lee |
| 2005/0273084 A1 | 12/2005 | Hinman et al. |
| 2005/0279804 A1 | 12/2005 | Scirica et al. |
| 2006/0011699 A1 | 1/2006 | Olson et al. |
| 2006/0016853 A1 | 1/2006 | Racenet |
| 2006/0025811 A1 | 2/2006 | Shelton |
| 2006/0025817 A1 | 2/2006 | Ortiz et al. |
| 2006/0047308 A1 | 3/2006 | Ortiz et al. |
| 2006/0049229 A1 | 3/2006 | Milliman et al. |

FOREIGN PATENT DOCUMENTS

| | | |
|---|---|---|
| EP | 0593920 | 4/1994 |
| JP | 09238947 | 9/1997 |

* cited by examiner

SURGICAL STAPLING APPARATUS

BACKGROUND

1. Technical Field

This present disclosure relates to a surgical stapling apparatus, and more particularly to an endoscopic surgical stapling apparatus for applying a plurality of surgical fasteners to body tissue.

2. Background of Related Art

Surgical devices wherein tissue is first grasped or clamped between opposing jaw structure and then joined by surgical fasteners are well known in the art. In some instruments, a knife is provided to cut the tissue which has been joined by the fasteners. The fasteners are typically in the form of surgical staples but two part polymeric fasteners can also be utilized.

Instruments for this purpose may include two elongated members which are respectively used to capture or clamp tissue. Typically, one of the members carries a staple cartridge that houses a plurality of staples arranged in at least two lateral rows while the other member has an anvil that defines a surface for forming the staple legs as the staples are driven from the staple cartridge. Generally, the stapling operation is effected by cam bars that travel longitudinally through the staple cartridge, with the cam bars acting upon staple pushers to sequentially eject the staples from the staple cartridge.

SUMMARY

The present disclosure relates to a surgical stapling apparatus including a frame, an endoscopic portion, a clamp handle, a firing handle, a tool assembly and a drive beam. The endoscopic portion extends distally from the frame. The clamp handle is disposed on the frame and in mechanical cooperation with a drive beam. The firing handle is disposed on the frame and in mechanical cooperation with a firing rod. The tool assembly includes an anvil, a cartridge assembly containing a plurality of surgical staples, and a camming surface. The tool assembly is supported adjacent a distal end of the endoscopic portion. The camming surface is arranged to actuate approximation of the anvil and the cartridge assembly with respect to one another. The drive beam has an opening therethrough. The firing rod is at least partially disposed in the opening of the drive beam and movable through the cartridge assembly to eject staples therefrom. The drive beam is configured to engage at least a portion of the camming surface of the tool assembly.

The present disclosure also relates to a surgical stapling apparatus including a frame, an endoscopic portion extending distally from the frame, a tool assembly, a drive member and a rod. The frame includes a first handle and a second handle. The tool assembly includes an anvil, a cartridge assembly and a camming surface. The tool assembly is supported adjacent a distal end of the endoscopic portion. The drive member is connected to the first handle and has a distal end configured to engage at least a portion of the camming surface. Actuation of the first handle moves the drive member distally into engagement with at least a portion of the camming surface to approximate the anvil and the cartridge assembly with respect to one another. The drive member has an opening therethrough. The rod is connected to the second handle so that manipulation of the second handle advances the rod distally through the opening of the drive member and ejects staples from the cartridge assembly.

The present disclosure also relates to a method of firing surgical fasteners. The method includes the step of providing a surgical stapling apparatus having a frame, an endoscopic portion extending distally from the frame, a first handle, a second handle, a tool assembly and a drive beam having an anvil and a cartridge assembly. The method also includes the step of actuating the first handle to move the drive beam to approximate the anvil and the cartridge assembly. The method further includes the step of actuating the second handle to move a firing rod through an opening in the drive beam.

DESCRIPTION OF THE DRAWINGS

Various embodiments of the presently disclosed surgical stapling apparatus are disclosed herein with reference to the drawings, wherein.

DETAILED DESCRIPTION OF EMBODIMENTS

Embodiments of the presently disclosed surgical stapling apparatus are described in detail with reference to the drawings wherein like numerals designate identical or corresponding elements in each of the several views. As is common in the art, the term "proximal" refers to that part or component closer to the user or operator, e.g., surgeon or physician, while the term "distal" refers to that part or component farther away from the user.

Figure 1:
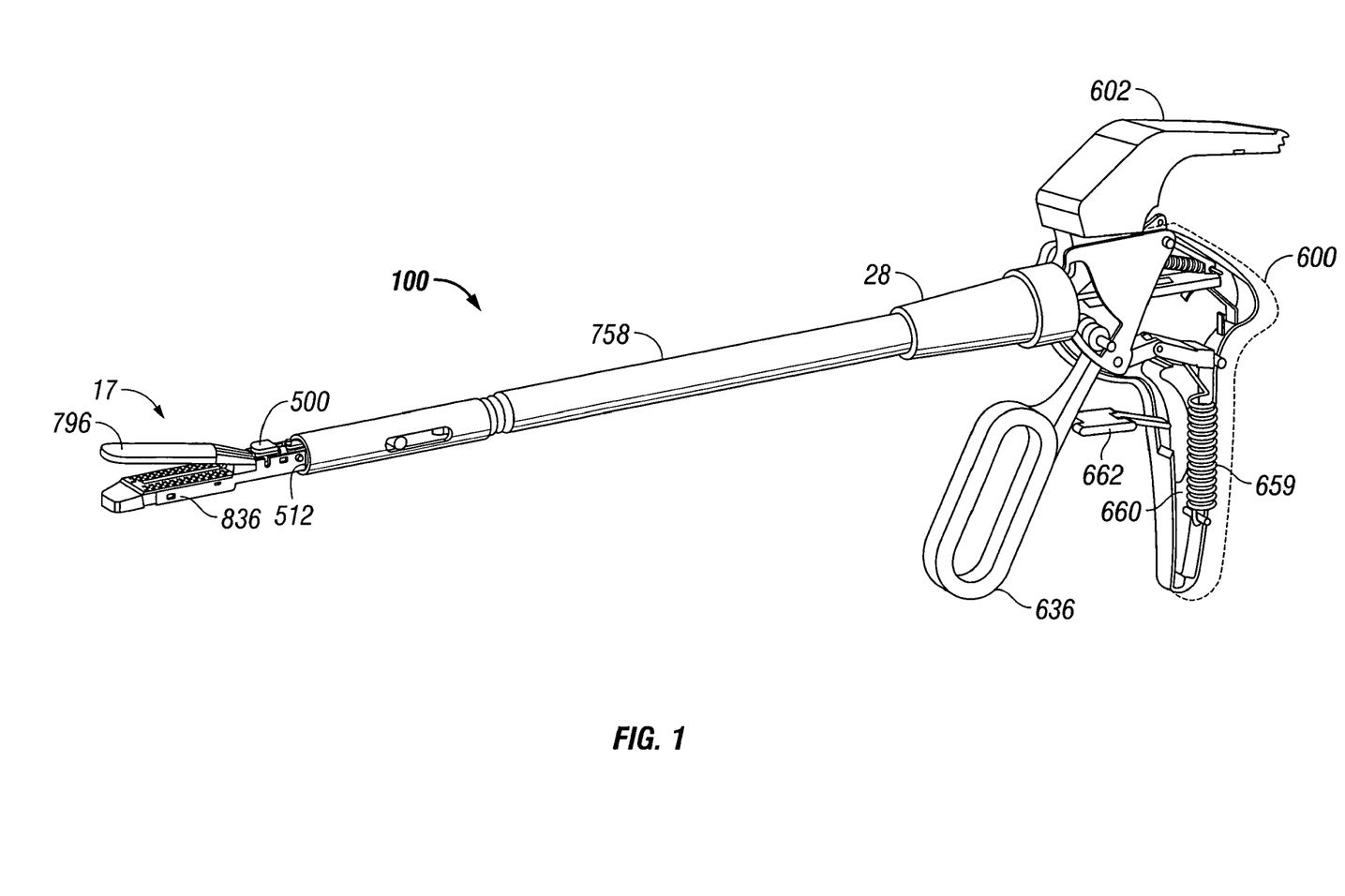
FIG. 1 illustrates a perspective, partial cutaway view of an assembled surgical stapling apparatus in accordance with an embodiment of the disclosure.

Referring to FIG. 1, an embodiment of a surgical stapling apparatus 100 of the present disclosure is illustrated. Surgical stapling apparatus 100 of this embodiment includes a frame 600, a clamp handle 602, a firing handle 636, an endoscopic portion 758 and a tool assembly 17. Endoscopic portion 758 defines a longitudinal axis for surgical stapling apparatus 100. Frame 600 is of an overall size and shape convenient for being held in the hand. Clamp handle 602 and firing handle 636 are both pivotally mounted to frame 600 for articulated movement between open and closed positions.

An example of various aspects of the present disclosure, including actuation of a surgical stapling apparatus, is disclosed in commonly-owned U.S. Pat. No. 6,953,139 to Milliman et al., the entire contents of which are hereby incorporated by reference herein.

Figure 8:
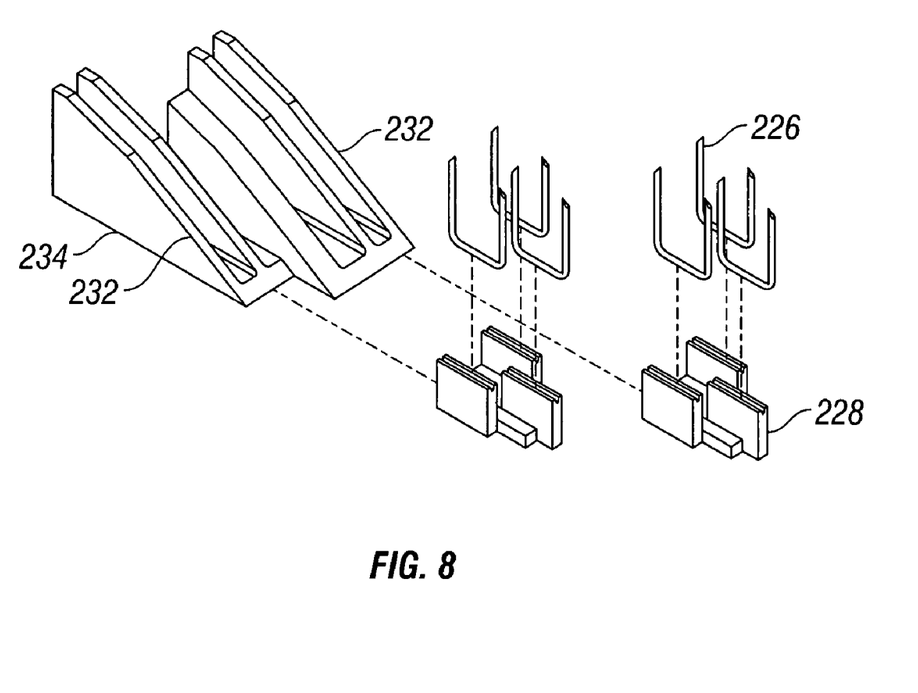
FIG. 8 is an enlarged perspective view of an actuation sled, pushers and fasteners in accordance with an embodiment of the present disclosure.

Tool assembly 17 includes an anvil 796 and a cartridge assembly 836. Anvil 796 and cartridge assembly 836 extend from a distal portion of endoscopic portion 758 and are pivotably secured in relation to each other. Anvil 796 includes a tissue-contacting surface with staple forming depressions thereon (not explicitly shown in the illustrated embodiments). Cartridge assembly 836 includes a plurality of surgical fasteners 226 (see FIG. 8) therein, which are ejectable through tissue and into anvil 796. A replaceable staple cartridge (not explicitly shown in the illustrated embodiments) may be used with surgical stapling apparatus 100 of FIG. 1. Such a replaceable staple cartridge may house a plurality of staples arranged in at least two lateral rows and may be mountable in a cartridge channel of cartridge assembly 836.

A portion of a drive assembly 120 is illustrated in FIGS. 2-6. Drive assembly 120 of this embodiment includes a drive beam 500 and a firing rod 550. The drive beam 500 is configured for longitudinal translation to approximate anvil 796 and cartridge assembly 836 with respect to one another. The firing rod 550 is configured for telescoping movement with respect to drive beam 500 by translating through an opening 502 in drive beam 500 to fire surgical fasteners 226 (e.g., staples) and/or to cut tissue.

Figure 2:
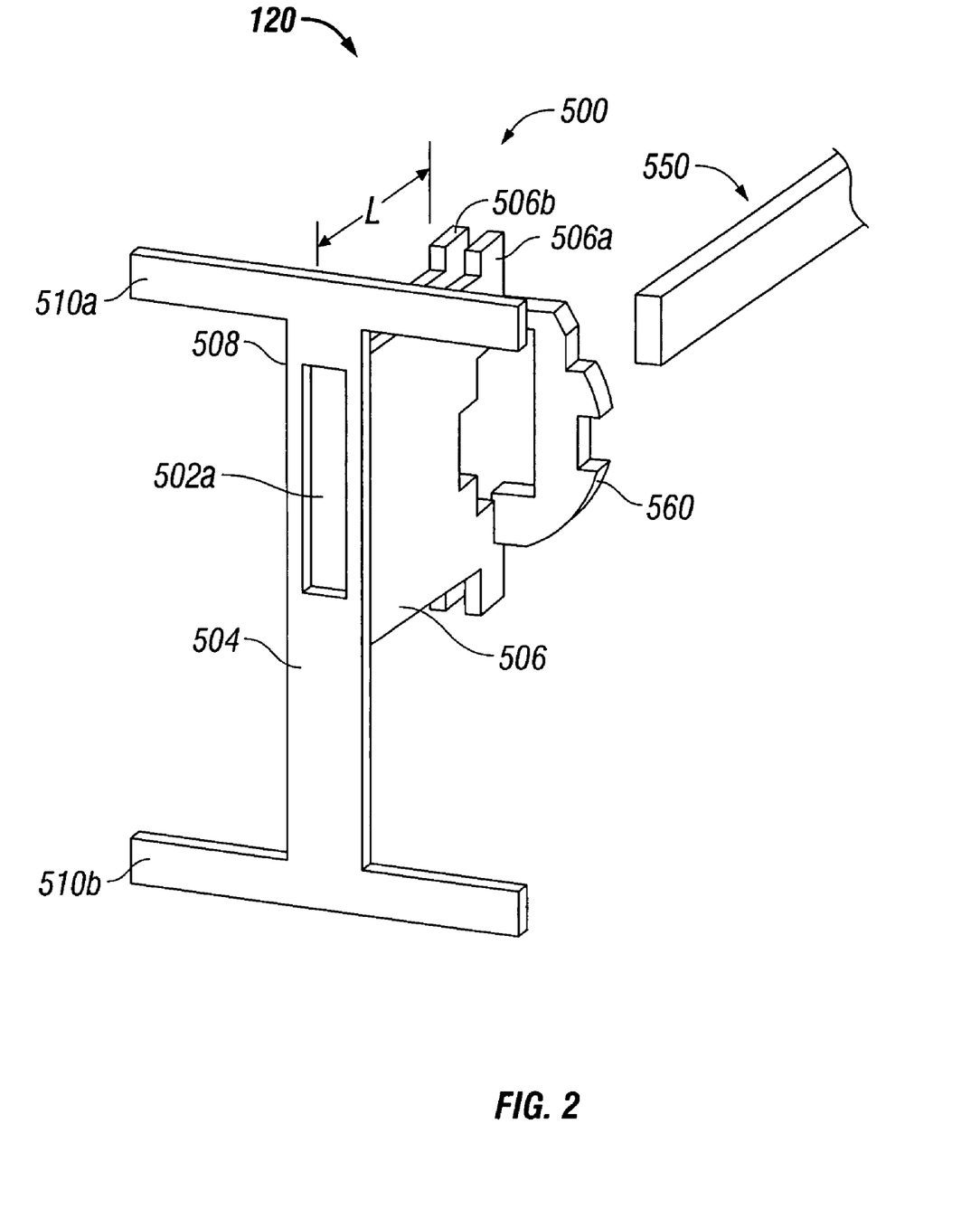
FIG. 2 is a perspective view of a drive assembly in accordance with an embodiment of the present disclosure.
Figure 3:
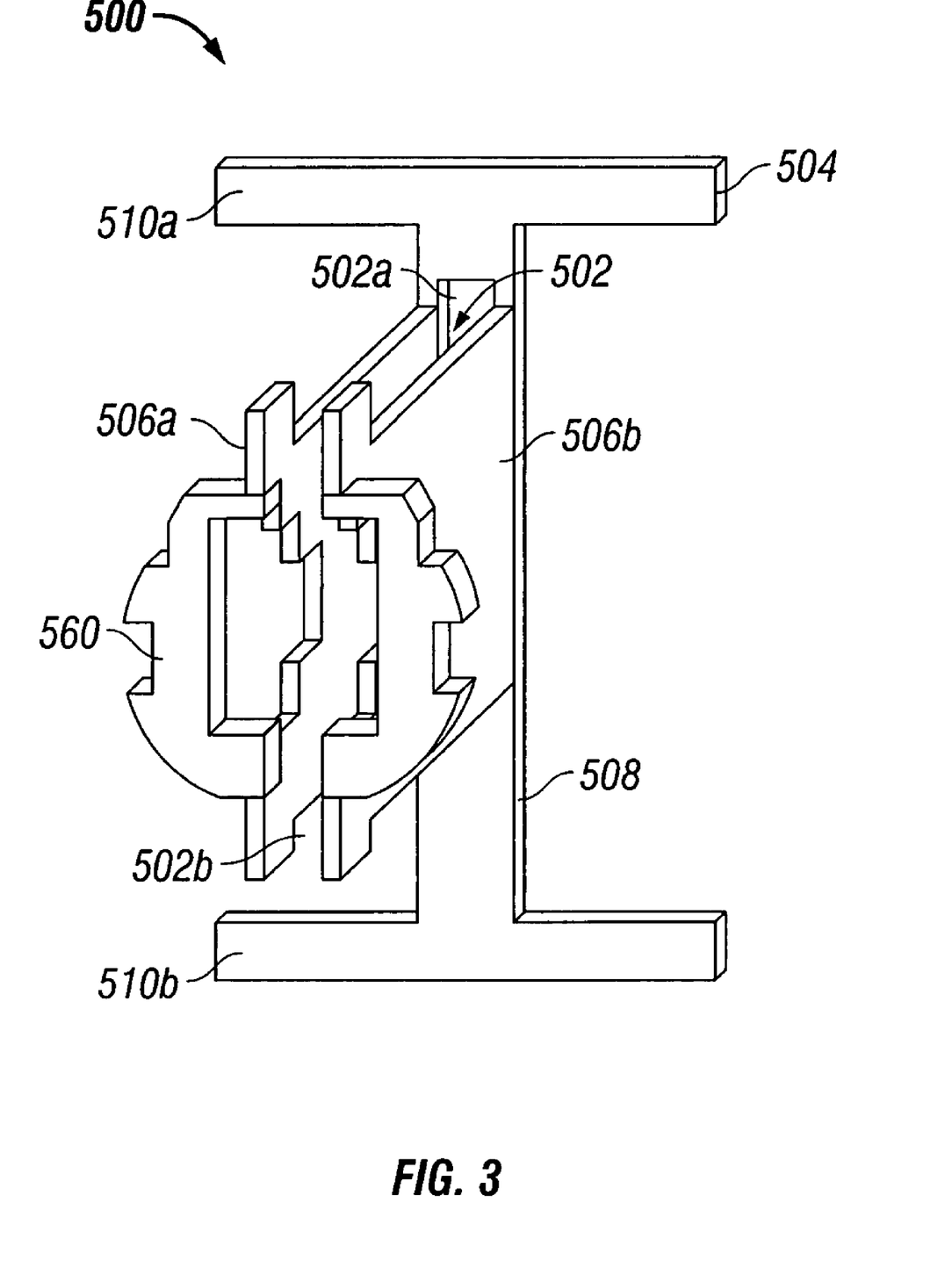
FIG. 3 is another perspective view of the drive assembly of FIG. 2.
Figure 4:
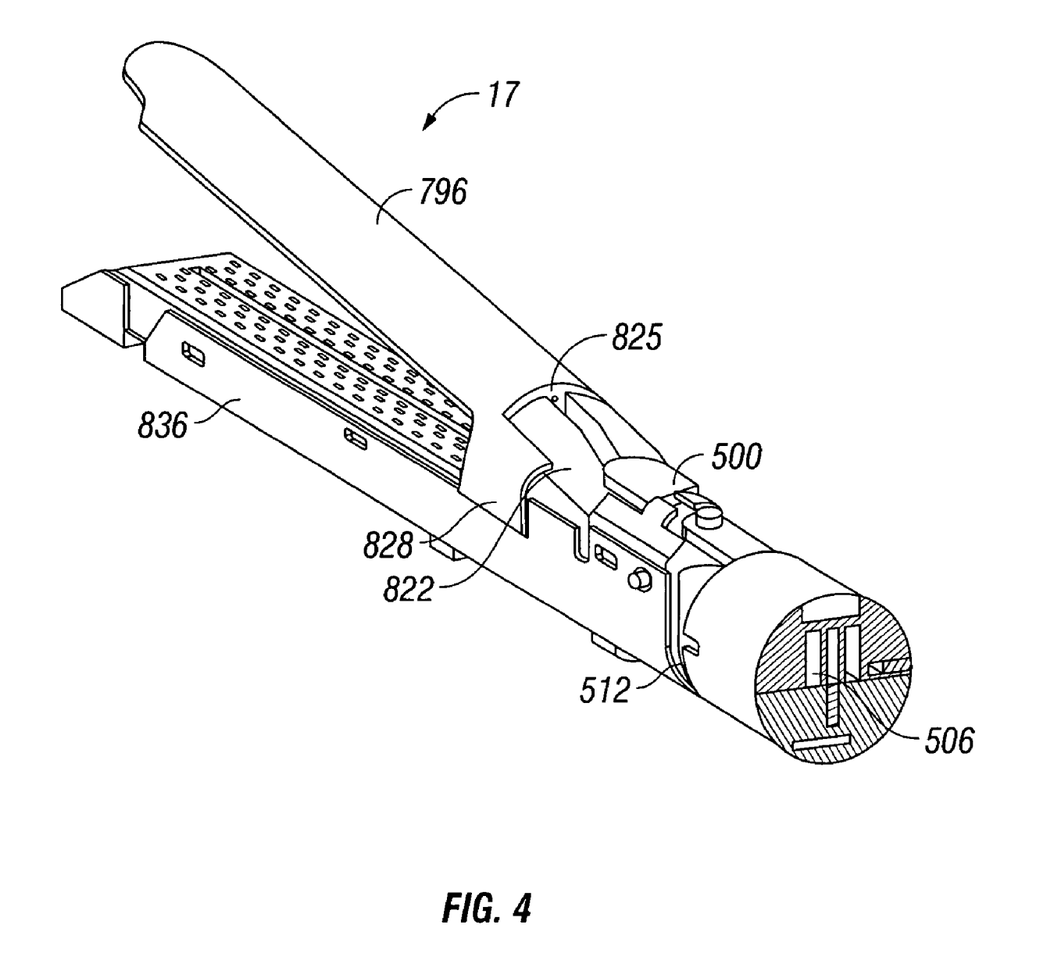
FIG. 4 is a perspective view of a portion of a tool assembly of the surgical stapling apparatus, illustrating a portion of the drive assembly of FIGS. 2 and 3.

More specifically, with reference to FIGS. 2 and 3, drive beam 500 includes a first portion 504 and a second portion 506. At least part of first portion 504 (e.g., a protrusion thereon) is configured for engaging anvil 796. First portion 504 of drive beam 500 has a vertical portion 508 and generally horizontal portions 510a and 510b. Horizontal portions 510a, 510b may be configured so that first portion 504 generally has an I-shaped cross-section. A first opening 502a of first portion 504 extends through vertical portion 508. Horizontal portion 510a is configured to engage upper camming surface 822 of anvil 796. Horizontal portion 510b is configured to engage cartridge assembly 836 (see FIG. 4). In the embodiment illustrated in FIGS. 2 and 3, second portion 506 of drive beam 500 extends proximally from first portion 504 and defines a second opening 502b, such that second opening 502b communicates with first opening 502a. Here, second portion 506 includes two generally rectangular portions 506a and 506b defining second opening 502b therebetween. It is envisioned that drive beam adapter 560 (FIGS. 2 and 3) is mechanically engaged with second portion 506 of drive beam 500 at the proximal end thereof. Drive beam adapter 560 may engage a suitable drive member (not explicitly shown in this embodiment) extending proximally through the endoscopic portion 758 of surgical stapling apparatus 100. Drive beam 500 is thereby connected to clamp handle 602 through a linkage to allow the movement of clamp handle 602 or firing handle 636 to be transferred to impart movement of drive beam 500.

The proximal end of firing rod 550 is attached directly or indirectly to firing handle 636 through a gear mechanism (see FIG. 1). Frame 600 and handles 602 and 636 may be constructed and arranged as disclosed in U.S. Pat. No. 5,318,221, the entire contents of which are hereby incorporated by reference herein. Other mechanisms for connecting firing handle 636 and/or clamp handle 602 to firing rod 550 and drive beam 500 may be used. For example, a toothed rack may be connected to firing rod 550 and driven by a pawl connected to firing handle 636.

It is envisioned that drive assembly 120 is arranged to allow tool assembly 17 to articulate. Tool assembly 17 is pivotably attached to endoscopic portion 758 at a pivot pin or flexible portion of endoscopic portion 758 to define an articulation junction 512. Second portion 506 of drive beam 500 is configured and arranged to flex around articulation junction 512 (FIGS. 1 and 4-6) through selection of materials for second portion 506 and firing rod 550, for example. Additionally or alternatively, second portion 506 an/or firing rod 550 may be comprised of a plurality of sheets or layers.

Firing rod 550 of the present embodiment is configured to fit through first and second parts 502a, 502b of opening 502. Firing rod 550 is capable of traveling through drive beam 500, and can be configured to travel through drive beam 500 when tool assembly 17 is articulated.

In a contemplated embodiment, drive beam 500 and/or firing rod 550 of the present disclosure may be made from a rigid, semi-rigid or flexible material (or combinations thereof) such as, for example, metal (e.g., stainless steel) or plastic. Further, firing rod 550 may include several portions that are telescopingly retractable and extendable with respect to each other. Shapes and configurations of firing rod 550 other than those shown are also contemplated by the present disclosure.

Figure 7:
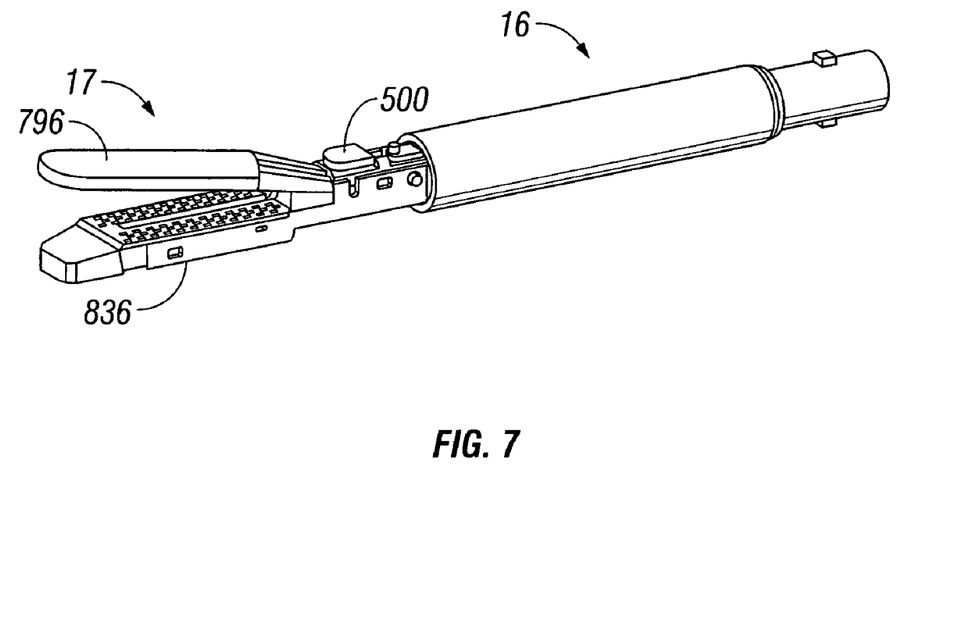
FIG. 7 is a perspective view of a disposable loading unit usable with the surgical stapling apparatus of FIG. 1.

It is envisioned that surgical stapling apparatus 100 is usable with a disposable loading unit (DLU) 16, such as the one illustrated in FIG. 7, which may have linear rows of staples between about 30 mm and about 60 mm. DLU 16 has a proximal body portion and a tool assembly attached to the proximal body portion. Other examples of disposable loading units for use with a surgical stapling apparatus are disclosed in commonly-owned U.S. Pat. No. 5,752,644 to Bolanos et al., the entire contents of which are hereby incorporated by reference herein.

OPERATION OF THE INSTRUMENT

In use, endoscopic portion 758 of surgical stapling apparatus 100 is inserted into a patient, possibly through an endoscopic tube. The endoscopic tube may be capable of maintaining a sealed pneumoperitoneum, with an internal sealing member of the housing further maintaining this seal despite introduction of surgical stapling apparatus 100 in accordance with the disclosure into the endoscopic tube. As a practical matter, the jaws of the instrument are closed for insertion into the endoscopic tube, either by closing anvil 796 and cartridge assembly 836 or by pivoting clamp handle 602.

After insertion into the endoscopic tube, anvil 796 and cartridge assembly 836 are returned to their first open position by opening clamp handle 602. Endoscopic portion 758 may be rotated to appropriately orient the instrument at the stapling site by manipulating a finger wheel, a sleeve, or rotation knob 28 (see FIG. 1). Rotation knob 28 may include a scalloped shape to facilitate engagement by a user's finger. Tissue stops 828 in anvil 796 may be included to prevent overinsertion of the tissue within tool assembly 17. Once the surgeon is satisfied with the placement of the tissue within tool assembly 17, tool assembly 17 is used to clamp the tissue.

To clamp tissue, clamp handle 602 (FIG. 1) is pivoted downward towards frame 600. Clamp handle 602 is connected drive beam adapter 560 so that drive beam 500 moves longitudinally when clamp handle 602 is pivoted closed. This distal longitudinal movement causes a portion of drive beam 500 to contact camming surface 822 of tool assembly 17 forcing anvil 796 towards cartridge assembly 836. Further details of the clamp handle 602 and drive member are disclosed in U.S. Pat. No. 5,318,221, the disclosure of which is hereby incorporated by reference herein.

When the surgeon is ready to emplace fasteners 226 and cut tissue, manual safety 662 may be disengaged from firing handle 636 and firing handle 636 is retracted. Firing handle 636 moves firing rod 550 longitudinally. An actuation sled 234 is positioned distally of the distal end of firing rod 550 so that the distal longitudinal movement of firing rod 550 advances actuation sled 234 in the distal direction. After actuation, firing handle 636 is released and returns to its original position, possibly with the help of a kicker spring 660 and a firing handle return spring 659. Further details of firing fasteners and the retraction of firing handle 636 are disclosed in U.S. Pat. No. 5,318,221 to Green et al., the entire contents of which are hereby incorporated by reference herein.

In another embodiment, firing handle 636 is actuated in a full stroke to close anvil 796 and cartridge assembly 836 and at least one subsequent stroke is utilized to deploy surgical fasteners 226 from cartridge assembly 836. In such embodiments, clamp handle 602 may not be necessary.

It is contemplated that tool assembly 17 of the present disclosure could be replaced with other interacting jaw members such as, for example, a pair of gripping jaw members for grasping and dissecting tissue as well as clamping jaw members for clamping off tissue or portions thereof. These interacting jaw members may include serrated portions to improve gripping/holding ability. Alternatively, the interacting jaw members may be provided with tissue contacting surfaces that may prevent or minimize trauma to held or clamped tissue. These interacting jaw members may be mounted in substantially the same way as the tool assembly 17 described herein with the exception that firing rod 550 may be used to drive functions other than surgical fasteners and/or knives.

Figure 5:
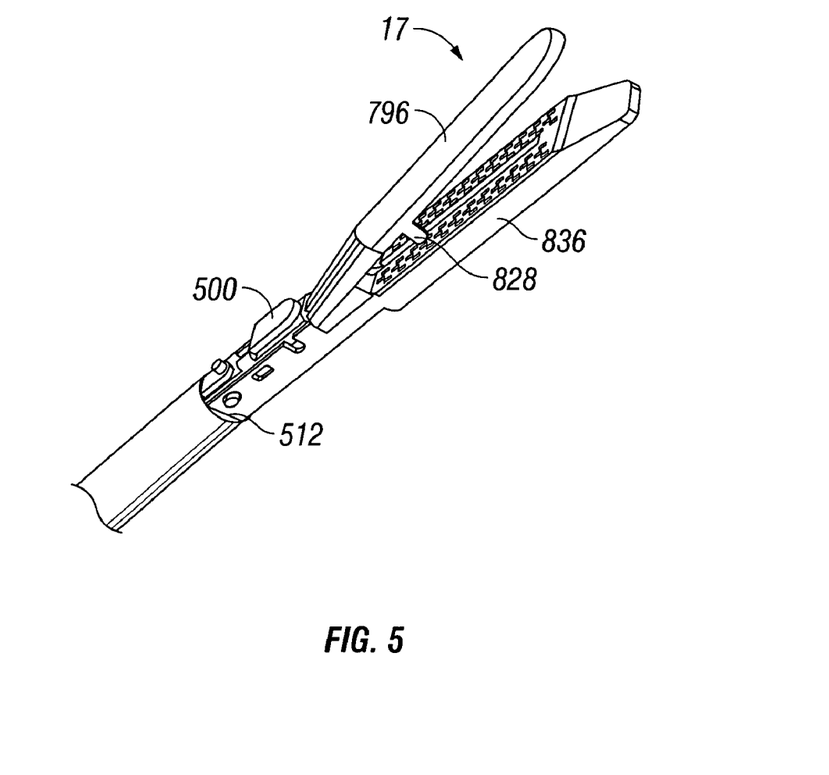
FIG. 5 is a perspective view of the tool assembly in accordance with an embodiment of the present disclosure in an open position, illustrating a portion of the drive assembly of FIGS. 2 and 3.
Figure 6:
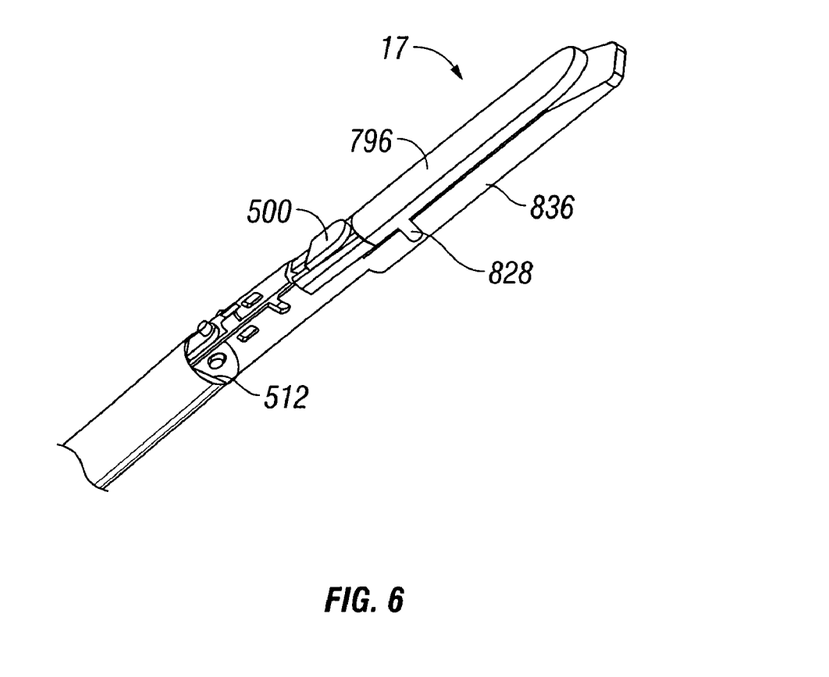
FIG. 6 is a perspective view of the tool assembly of FIG. 5 in a closed position, illustrating a portion of the drive assembly of FIGS. 2 and 3.

In a disclosed embodiment, a user pivots clamp handle 602 downward to advance a suitable drive member and drive beam adapter 560, thus causing drive beam 500 to travel distally and approximate anvil 796 and cartridge assembly 836. FIG. 5 illustrates tool assembly 17 prior to drive beam 500 traveling distally. FIG. 6 shows tool assembly 17 approximated after drive beam 500 has moved distally. While FIGS. 5 and 6 illustrate drive beam 500 moving anvil 796 with respect to cartridge assembly 836, it is envisioned and within the scope of the present disclosure that one or both of anvil 796 and cartridge assembly 836 is movable, so that drive beam 500 moves cartridge assembly 836 only, or moves both cartridge assembly 836 and anvil 796. It is also envisioned that, in lieu of clamp handle 602, a partial stroke of firing handle 636 may advance drive beam 500 a sufficient distance to approximate tool assembly 17, or a full stroke of firing handle 636 approximates tool assembly 17.

More specifically, upon depression of clamp handle 602 (or partial actuation of firing handle 636), drive beam 500 travels distally. Horizontal portions 510a and 510b of drive beam 500 travel a distance so that horizontal portion 510a contacts camming surface 822 of anvil 796, thus approximating anvil 796 and cartridge assembly 836 while horizontal portion 510b engages cartridge assembly 836. Drive beam 500 continues distally until it contacts a lip 825 of anvil 796. In such an embodiment, a portion of drive beam 500 may be approximately aligned with a tissue stop 828 when lip 825 is contacted. Upon contacting lip 825, drive beam 500 ceases distal travel.

Firing rod 550 translates through opening 502 of drive beam 500, either before, during or after drive beam 500 is translated distally. It is envisioned and within the scope of the present disclosure that firing rod 550 is a rectangular band, circular, or other shape in cross-section. In such an embodiment, firing rod 550 may be appropriately dimensioned to slidingly fit within opening 502.

Once appropriately positioned and clamped on tissue, surgical stapling apparatus 100 is ready to be fired. To fire surgical stapling apparatus 100 and thus eject fasteners 226 into tissue, firing handle 636 is actuated. Actuation of firing handle 636 translates firing rod 550 through second portion 506 of drive beam 500 (as discussed above), through first portion 504 of drive beam 500 and into actuation sled 234 (FIG. 8) (or another suitable structure such as cam bars), which causes fasteners 226 to be ejected from cartridge assembly 836 and into tissue. More specifically and with reference to FIG. 8, during operation of surgical stapling apparatus 100 according to an embodiment of the disclosure, actuation sled 234 translates through longitudinal slots of cartridge assembly 836 and cam surfaces 232 of actuation sled 234 are advanced into contact (e.g., sequential contact) with pushers 228. This movement causes pushers 228 to translate substantially vertically within the longitudinal slots and urges fasteners 226 into staple forming depressions of anvil 796. Desirably, a knife blade is disposed on the distal end of firing rod 550 or on actuation sled 234, so that the knife blade is proximal of cam surfaces 232 of actuation sled 234.

While not explicitly described above, it is envisioned that a replaceable staple cartridge may be used with surgical stapling apparatus 100.

It will be understood that various modifications can be made to the various embodiments of the present disclosure herein disclosed without departing from the spirit and scope thereof. For example, various sizes of the instrument are contemplated, as well as various types of construction materials. Also, various modifications may be made in the configuration of the parts. As another example, a knife may be provided with a single-use cartridge, thus allowing a new knife to be used for each firing of the surgical stapling apparatus. Therefore the above description should not be construed as limiting the disclosure but merely as exemplifications of various embodiments thereof. Those skilled in the art will envision other modifications within the scope and spirit of the present disclosure as defined by the claims appended hereto.

The invention claimed is:

1. A surgical stapling apparatus, comprising:
   a frame;
   an endoscopic portion extending distally from the frame and defining a longitudinal axis;
   a clamp handle disposed on the frame and in mechanical cooperation with a drive member;
   a firing handle disposed on the frame and in mechanical cooperation with at least one firing rod;
   a tool assembly including an anvil, a cartridge assembly and a camming surface, the tool assembly being supported adjacent a distal end of the endoscopic portion; and
   a drive beam having a proximal engagement portion disposed adjacent a proximal end thereof and being configured to engage a distal portion of the drive member and having an upper flange portion and a lower flange portion disposed adjacent a distal end of the drive beam, the drive beam configured so that one of the upper flange portion and the lower flange portion engages at least a portion of the camming surface of the tool assembly, the drive beam having a vertical member, whereby actuation of the clamp handle moves the drive beam distally into engagement with at least a portion of the camming surface to approximate the anvil and the cartridge assembly; the vertical member of the drive beam having an opening therethrough extending from the proximal end through the distal end and whereby actuation of the firing handle moves the at least one firing rod through the opening to eject surgical fasteners from the cartridge assembly;
   wherein a portion of the drive beam has a cross section including a vertical portion and two horizontal portions;
   wherein the opening of the drive beam extends through the vertical portion of the cross-section of the drive beam;
   wherein the vertical portion is substantially perpendicular to the longitudinal axis;
   wherein each of the upper flange portion and the lower flange portion is planar and parallel to one another;

wherein one of the upper flange portion and the lower flange portion is configured to engage the anvil and wherein the other flange portion is configured to engage the cartridge assembly.

2. The surgical stapling apparatus according to claim 1, wherein at least a portion of the drive beam is made of a flexible material.

3. The surgical stapling apparatus according to claim 1, wherein at least a portion of the drive beam is made of a material selected from the group consisting of plastic and metal.

4. The surgical stapling apparatus according to claim 1, wherein at least a portion of the at least one firing rod is made of a flexible material.

5. The surgical stapling apparatus according to claim 1, wherein at least a portion of the at least one firing rod is made of a material selected from the group consisting of plastic and metal.

6. The surgical stapling apparatus according to claim 1, wherein the tool assembly includes a tissue stop disposed adjacent at least a portion of the camming surface thereof.

7. The surgical stapling apparatus according to claim 1, wherein the tool assembly is part of a disposable loading unit.

8. The surgical stapling apparatus according to claim 1, wherein each of the horizontal portions is disposed transverse to the longitudinal axis.

9. The surgical stapling apparatus according to claim 1, wherein each of the upper flange portion and the lower flange portion extends laterally from the vertical member of the drive beam.

10. A surgical stapling apparatus, comprising:
a frame having a first handle and a second handle;
an endoscopic portion extending distally from the frame;
a tool assembly including an anvil, a cartridge assembly and a camming surface disposed on the anvil, the tool assembly being supported adjacent a distal end of the endoscopic portion;
a drive beam connected to the first handle, the drive beam having a distal end including an upper flange portion and a lower flange portion, the drive beam configured so that one of the upper flange portion and the lower flange portion engages at least a portion of the camming surface of the tool assembly, the drive beam having a vertical member, whereby actuation of the first handle moves the drive beam distally into engagement with at least a portion of the camming surface to approximate the anvil and the cartridge assembly with respect to one another, the drive beam having an opening therethrough;
a rod connected to the second handle so that manipulation of the second handle advances the rod distally through the opening of the vertical member of the drive beam and ejects staples from the cartridge assembly.

11. The surgical stapling apparatus according to claim 10, wherein at least one of the upper flange portion and the lower flange portion of the drive beam is configured to engage the cartridge assembly.

12. The surgical stapling apparatus according to claim 10, wherein the tool assembly is pivotably attached to the endoscopic portion.

13. The surgical stapling apparatus according to claim 10, wherein at least a portion of the rod is flexible to allow the tool assembly to articulate.

14. The surgical stapling apparatus according to claim 10, wherein at least a portion of the drive beam is flexible to allow the tool assembly to articulate.

15. The surgical stapling apparatus according to claim 10, wherein the tool assembly includes a tissue stop disposed adjacent at least a portion of the camming surface thereof.

16. The surgical stapling apparatus according to claim 10, wherein the tool assembly is part of a disposable loading unit, the disposable loading unit including a proximal body portion and the tool assembly attached to the proximal body portion.

17. The surgical stapling apparatus according to claim 10, wherein each of the upper flange portion and the lower flange portion extends laterally from the vertical member of the drive beam.

18. A method of firing surgical fasteners, comprising:
providing a surgical stapling apparatus, including:
a frame;
an endoscopic portion extending distally from the frame;
a first handle disposed on the frame and in mechanical cooperation with a drive member;
a second handle disposed on the frame and in mechanical cooperation with at least one firing rod;
a tool assembly including an anvil, a cartridge assembly and a camming surface disposed on the anvil, the tool assembly being supported adjacent a distal end of the endoscopic portion; and
a drive beam configured to engage a distal portion of the drive member and having a flange configured to engage at least a portion of the camming surface of the tool assembly;
actuating the first handle to move the drive beam distally into engagement with at least a portion of the camming surface of the anvil to approximate the anvil and the cartridge assembly; and
actuating the second handle to move the firing rod through an opening in a vertical member of the drive beam.

19. The method according to claim 18, wherein at least a portion of the drive beam is made of a flexible material.

20. The method according to claim 18, wherein a portion of the drive beam has a cross section including a vertical portion and two horizontal portions.

21. The method according to claim 20, wherein the opening of the drive beam extends through the vertical portion of the cross-section of the drive beam.

22. The method according to claim 18, wherein at least a portion of the at least one firing rod is made of a flexible material.

* * * * *